(12) United States Patent
Kals

(10) Patent No.: US 9,320,896 B2
(45) Date of Patent: Apr. 26, 2016

(54) ACCELERATED FITTING OF COCHLEAR IMPLANTS BASED ON CURRENT SPREAD

(75) Inventor: Mathias Kals, Innsbruck (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 739 days.

(21) Appl. No.: 13/233,148

(22) Filed: Sep. 15, 2011

(65) Prior Publication Data

US 2012/0065705 A1    Mar. 15, 2012

Related U.S. Application Data

(60) Provisional application No. 61/382,996, filed on Sep. 15, 2010.

(51) Int. Cl.
*A61N 1/36*    (2006.01)

(52) U.S. Cl.
CPC .................................. *A61N 1/36032* (2013.01)

(58) Field of Classification Search
None
See application file for complete search history.

(56) References Cited

U.S. PATENT DOCUMENTS

| | | | |
|---|---|---|---|
| 4,284,856 A | 8/1981 | Hochmair et al. | 179/107 E |
| 4,515,158 A | 5/1985 | Patrick et al. | 128/419 R |
| 5,601,617 A | 2/1997 | Loeb et al. | 607/56 |
| 5,626,629 A | 5/1997 | Faltys et al. | 607/57 |
| 5,749,912 A | 5/1998 | Zhang et al. | 607/57 |
| 5,938,691 A | 8/1999 | Schulman et al. | 607/57 |
| 6,175,767 B1 | 1/2001 | Doyle, Sr. | 607/57 |
| 6,219,580 B1 | 4/2001 | Faltys et al. | 607/57 |
| 6,289,247 B1 | 9/2001 | Faltys et al. | 607/57 |
| 6,295,472 B1 | 9/2001 | Rubinstein et al. | 607/55 |
| 6,584,525 B1 | 6/2003 | Klingman | 710/118 |
| 6,594,525 B1 | 7/2003 | Zierhofer | 607/57 |
| 6,600,955 B1 | 7/2003 | Zierhofer | 607/57 |
| 6,778,858 B1 | 8/2004 | Peeters | 607/57 |
| 6,826,430 B2 | 11/2004 | Faltys et al. | 607/137 |
| 7,110,821 B1 * | 9/2006 | Ross | 607/57 |
| 7,209,789 B2 | 4/2007 | Zierhofer | 607/57 |
| 7,515,966 B1 | 4/2009 | Litvak et al. | 607/57 |
| 2001/0031909 A1 | 10/2001 | Faltys et al. | 600/25 |
| 2004/0082985 A1 | 4/2004 | Faltys et al. | 607/116 |
| 2005/0107843 A1 | 5/2005 | McDermott et al. | 607/57 |

(Continued)

FOREIGN PATENT DOCUMENTS

| | | | |
|---|---|---|---|
| WO | WO 99/35882 | 7/1999 | H04R 25/00 |
| WO | WO 99/49815 | 10/1999 | A61F 2/18 |

(Continued)

OTHER PUBLICATIONS

Kral, A., et al, "Spatial resolution of cochlear implants: the electrical field and excitation of auditory afferents", *Hearing Research*, vol. 121 (1998, pp. 11-28.

(Continued)

*Primary Examiner* — Erica Lee

(74) *Attorney, Agent, or Firm* — Sunstein Kann Murphy & Timbers LLP

(57) ABSTRACT

Approaches are described for fitting an implanted cochlear implant electrode array having stimulation electrodes to the implanted patient. A first unfit stimulation electrode is fit to the patient by determining a most comfortable loudness (MCL) value. Then an MCL value is determined for each remaining unfit stimulation electrode starting from an initial fitting current based on current spread characteristics of at least one already fit stimulation electrode.

12 Claims, 3 Drawing Sheets

(56) References Cited

U.S. PATENT DOCUMENTS

| | | | |
|---|---|---|---|
| 2005/0203589 A1 | 9/2005 | Zierhofer | 607/57 |
| 2006/0052841 A1 | 3/2006 | Daly et al. | 607/57 |
| 2006/0080087 A1 | 4/2006 | Vandali et al. | 704/207 |
| 2006/0227986 A1 | 10/2006 | Swanson et al. | 381/312 |
| 2006/0235332 A1* | 10/2006 | Smoorenburg | 600/559 |
| 2006/0247735 A1* | 11/2006 | Honert | 607/57 |
| 2006/0265061 A1 | 11/2006 | Kwon et al. | 623/10 |
| 2007/0156202 A1 | 7/2007 | Zierhofer | 607/57 |
| 2007/0225776 A1 | 9/2007 | Fritsch et al. | 607/57 |
| 2009/0036962 A1* | 2/2009 | Zierhofer | 607/137 |
| 2009/0043359 A1 | 2/2009 | Smoorenburg | 607/57 |
| 2010/0198301 A1* | 8/2010 | Smith | 607/57 |

FOREIGN PATENT DOCUMENTS

| | | | | |
|---|---|---|---|---|
| WO | WO 01/19135 | 3/2001 | | H04R 25/00 |
| WO | WO 01/19304 | 3/2001 | | A61F 11/04 |
| WO | WO 2005/113064 | 12/2005 | | A61N 1/36 |
| WO | WO 2006/119069 | 11/2006 | | A61N 1/32 |

OTHER PUBLICATIONS

Loizou, P.C., "Signal Processing for Cochlear Prosthesis: A Tutorial Review", *IEEE*, Jan. 1997, pp. 881-885; 0-7803-3694-1/97.

Loizou, P.C., "Signal-Processing Techniques for Cochlear Implants", *IEEE Engineering in Medicine and Biology*, May/Jun. 1999, pp. 34-46.

McKay, Colette, et al, "The effect of rate of stimulation on perception of spectral shape by cochlear implantees", *Journal of Acoustical Society of America*, AIP/Acoustical Society of America, Melville, NY, US, vol. 118; No. 1; Jan. 1, 2005, pp. 386-392; XP012073185; ISSN: 001-4966.

Secker-Walker, H., et al, "Time-domain analysis of auditory-nerve-fiber firing rates", *J. Acoust. Soc. Am.* 88(3), pp. 1427-1436 (1990).

Wilson, B.S., et al, "Comparative Studies of Speech Processing Strategies for Cochlear Implants", *Laryngoscope*, vol. 96, No. 10, pp. 1068-1077, Oct. 1988.

Wilson, B. S., et al, "Better speech recognition with cochlear implants", *Nature*, vol. 352, pp. 236-238, Jul. 18, 1991.

Wilson, B. S., et al, "Seventh Quarterly Progress Report; Speech Processors for Auditory Prostheses", *Center for Auditory Prosthesis Research*, pp. 1-69, 1994.

Wilson, B. S., et al, "Temporal Representations With Cochlear Implants", *The American Journal of Otology*, 18:530-534, 1997.

Ziese, M., et al, "Speech Understanding with the CIS and the n-of-m Strategy in the MED-EL COMBI 40+System", *ORL*, 2000;62:321-329.

European Patent Office, Officer Karin Sigurd, International Search Report and Written Opinion, PCT/US2011/051688, date of mailing Nov. 28, 2011, 12 pages.

* cited by examiner

ACCELERATED FITTING OF COCHLEAR IMPLANTS BASED ON CURRENT SPREAD

This application claims priority from U.S. Provisional Patent Application 61/382,996, filed Sep. 15, 2010, which is incorporated herein by reference.

TECHNICAL FIELD

The present invention relates to medical implants, and more specifically to fit customization in audio prosthesis systems such as cochlear implant systems.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

Cochlear implant systems employ stimulation strategies that provide high-rate pulsatile stimuli in multi-channel electrode arrays. One specific example is the "Continuous Interleaved Sampling (CIS)"-strategy, as described by Wilson et al., *Better Speech Recognition With Cochlear Implants*, Nature, vol. 352:236-238 (1991), which is incorporated herein by reference. For CIS, symmetrical biphasic current pulses are used, which are strictly non-overlapping in time. The rate per channel typically is higher than 800 pulses/sec. Other stimulation strategies may be based on simultaneous activation of electrode currents. These approaches have proven to be successful in giving high levels of speech recognition.

For an audio prosthesis such as a cochlear implant to work correctly, some patient-specific operating parameters need to be determined in a fit adjustment procedure where the type and number of operating parameters are device dependent and stimulation strategy dependent. Possible patient-specific operating parameters for a cochlear implant include:

$THR_1$ (lower detection threshold of stimulation amplitude) for Electrode 1
$MCL_1$ (most comfortable loudness) for Electrode 1
Phase Duration for Electrode 1
$THR_2$ for Electrode 2
$MCL_2$ for Electrode 2
Phase Duration for Electrode 2
. . .
Pulse Rate
Number of fine structure channels
Compression
Parameters of frequency→electrode mapping
Parameters describing the electrical field distribution One approach for an objective measurement of MCLs and THLs is based on the measurement of the EAPs (Electrically Evoked Action Potentials), as described by Gantz et al., *Intraoperative Measures of Electrically Evoked Auditory Nerve Compound Action Potentials*, American Journal of Otology 15 (2):137-144 (1994), which is incorporated herein by reference. In this approach, a recording electrode in the scala tympani of the inner ear is used. The overall response of the auditory nerve to an electrical stimulus is measured very close to the position of the nerve excitation. This neural response is caused by the super-position of single neural responses at the outside of the axon membranes. The amplitude of the EAP at the measurement position is between 10 μV and 1800 μV.

One common method for fit adjustment is to behaviorally find the threshold (THR) and most comfortable loudness (MCL) value for each separate stimulation electrode. See for example, Rätz, *Fitting Guide for First Fitting with MAESTRO 2.0*, MED-EL, Fürstenweg 77a, 6020 Innsbruck, 1.0 Edition, 2007. AW 5420 Rev. 1.0 (English_EU); incorporated herein by reference. Other alternatives/extensions are sometimes used with a reduced set of operating parameters; e.g. as suggested by Smoorenburg, *Cochlear Implant Ear Marks*, University Medical Centre Utrecht, 2006; U.S. Patent Application 20060235332; which are incorporated herein by reference. Typically each stimulation channel is fitted separately without using the information from already fitted channels. The stimulation current on a given electrode typically is increased in steps from zero until the MCL (most comfortable loudness) is reached.

These tests are quite time consuming and several approaches have been developed to accelerate the fitting process. One approach uses a flat map, i.e. the same MCL value on all stimulation channels so that only one channel needs to be fitted. Another approach is to increase stimulation current during fitting on N adjacent channels simultaneously from zero onwards and thereby fit N adjacent channels simultaneously. These and similar approaches do save time, however, they have the disadvantage ignoring channel-specific particularities such as markedly different MCL values on different channels. A third fitting approach does not start from zero current when fitting a channel, but rather from some other fixed initial value, but this initial value can sometimes be too high or too low for some channels.

SUMMARY

Embodiments of the present invention are directed to fitting an implanted cochlear implant electrode array having stimulation electrodes to the implanted patient. A first unfit stimulation electrode is fit to the patient by determining a most comfortable loudness (MCL) value. Then an MCL value is determined for each remaining unfit stimulation electrode starting from an initial fitting current based on current spread characteristics of at least one already fit stimulation electrode.

The current spread characteristics may be represented by an exponential decay function and/or may be based on a voltage profile measured along the electrode array. The initial fitting current may further be based on a fixed percentage of the MCL value for an already fit stimulation electrode. The at least one already fit stimulation electrode may be a next more apical or a next more basal stimulation electrode.

Embodiments also include a cochlear implant fitting system using a method according to any of the above, and a computer program product implemented in a computer readable storage medium for fitting an implanted electrode of a cochlear implant to an implanted patient and including program code for performing a method according to any of the above.

DETAILED DESCRIPTION

Embodiments of the present invention are directed to a method and a system which provides a starting point for the fitting of each stimulation electrode. Already fit stimulation electrode channels are used to quickly and accurately determine MCL values for each remaining stimulation electrodes taking into account current spread characteristics of the cochlea.

Figure 1:
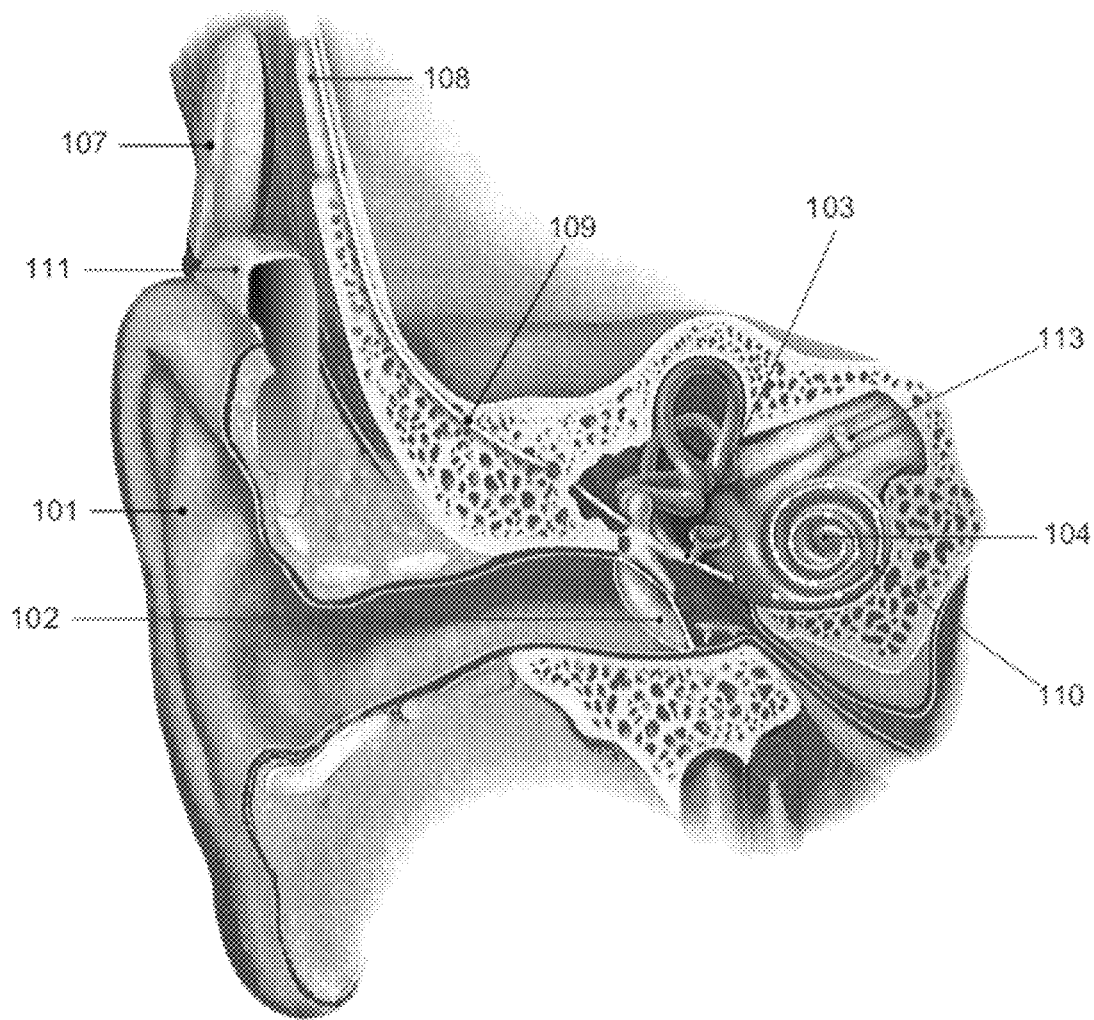
FIG. 1 shows anatomical structures in a human ear having a cochlear implant system.
Figure 2:
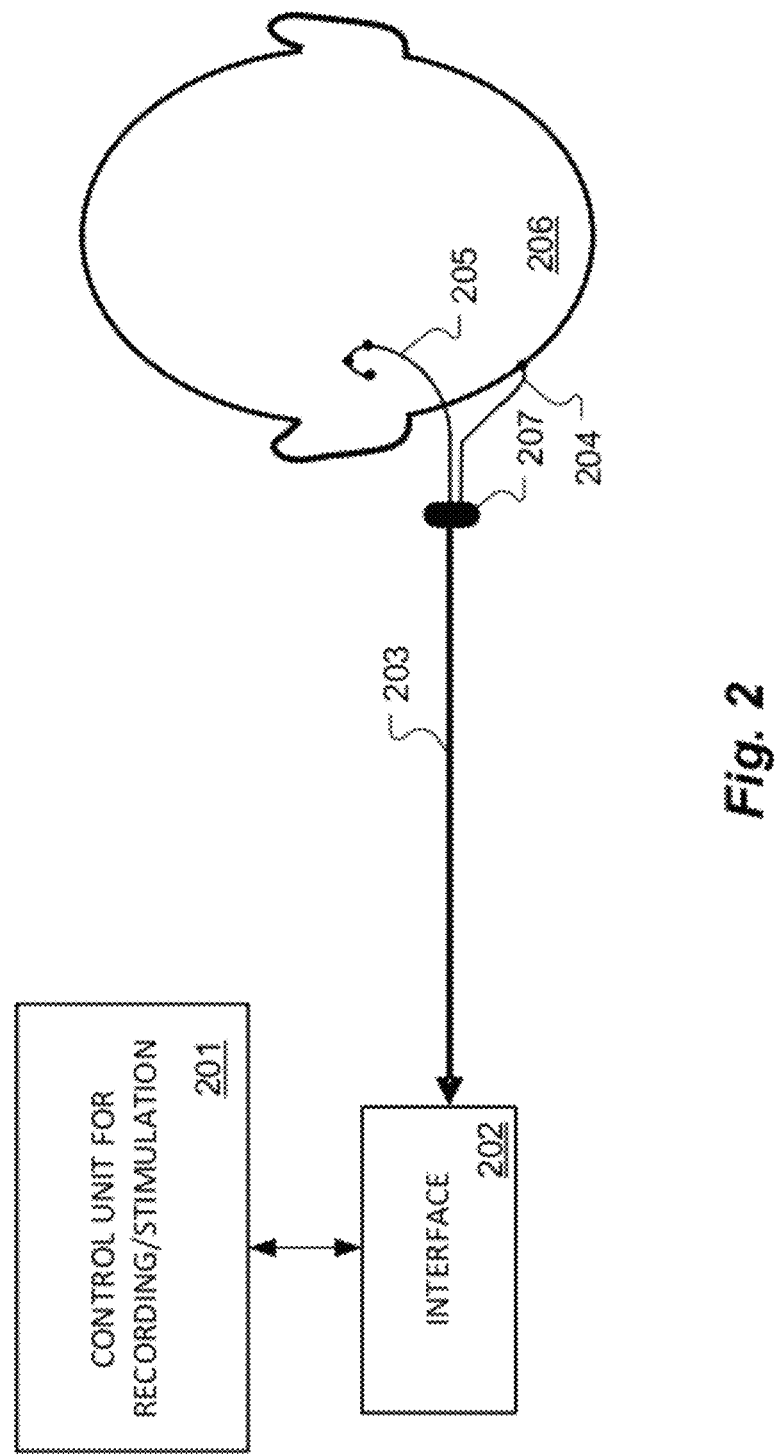
FIG. 2 shows a block diagram of a cochlear implant fitting system according to one specific embodiment of the present invention.

FIG. 2 shows a block diagram of a cochlear implant fitting system according to one specific embodiment of the present invention. Control Unit 201 for Recording and Stimulation, for example, a Med-El Maestro CI system, generates stimulation signals and analyzes response measurements. Connected to the Control Unit 201 is an Interface Box 202, for example, a Diagnostic Interface System such as the DIB II conventionally used with the Maestro CI system that formats and distributes the input and output signals between the Control Unit 201 and the system components implanted in the Patient 206. For example, as shown in FIG. 2, there may be an Interface Lead 203 connected at one end to the Interface Box 202 and at the other end having Electrode Plug 207 that then divides into a Cochlear Implant Electrode 204 and an Extra-Cochlear Ground Electrode 205. After delivering a stimulation pulse, a Cochlear Implant Electrode 204 may be used as a sensing element to determine current and voltage characteristics of the adjacent tissue, for example, for use measuring current spread.

Control Unit 201 fits a first unfit Cochlear Implant Electrode 204 to the patient by determining a most comfortable loudness (MCL) value for that electrode. Control Unit 201 then determines an MCL value for each remaining unfit Cochlear Implant Electrode 204 starting from an initial fitting current based on current spread characteristics of at least one already fit Cochlear Implant Electrode 204.

US 2009036962 describes one specific possible current spread model where the spread decays approximately exponentially and can be expressed by:

$$I(x) = I\exp\left(-\frac{x}{\lambda}\right) \qquad (\text{Eq. 1})$$

where I(x) is the current at some distance x from stimulus I, and λ is a decay constant. For electrode arrays with equidistant distance d between the electrode contacts, the decay on next neighboring electrode can be expressed as in Equation 2 by an exponential function with base α:

$$\frac{I(x=d)}{I(0)} = \exp\left(-\frac{d}{\lambda}\right) = \alpha \qquad \text{Eq. (2)}$$

By reason of the geometrical structure (narrowing tube), two exponential constants in directions apical (α) and basal (β) respectively model the electrode current spread. The resulting current at the location of electrode m when electrode n is stimulated with current $I_n$ is given by:

$$I_{n,m} = I_n \alpha^{|n-m|} \text{ for } m<n, \text{ and}$$

$$I_{n,m} = I_n \beta^{|n-m|} \text{ for } m \geq n \qquad \text{Eq. (3)}$$

For example, for an electrode spacing of d=2.4 mm, α and β are typically around 0.75 and 0.70 respectively. Telemetry measurements can be taken inside the cochlea to measure the voltage profile along the electrode array when a stimulus pulse is applied on the electrode array. The two decay constants are reflected in the measured voltage profile and can then be assessed in each individual patient.

After fitting of the first stimulation electrode (e.g., by starting from zero), the next (or more distant) apical or basal electrode is fitted by starting at the corresponding level obtained from the current spread of the previous fitted electrode rather than from zero or any other (arbitrarily) estimated level. This can be done directly when pulse phase durations are identical. If that is not the case, then rather than current levels as such, charge levels, the product of current I and pulse phase duration T can be used as shown in Equation 4 to take into account different pulse phase durations on individual electrode channels:

$$Q=IT \qquad \text{Eq. (4)}$$

Figure 3:
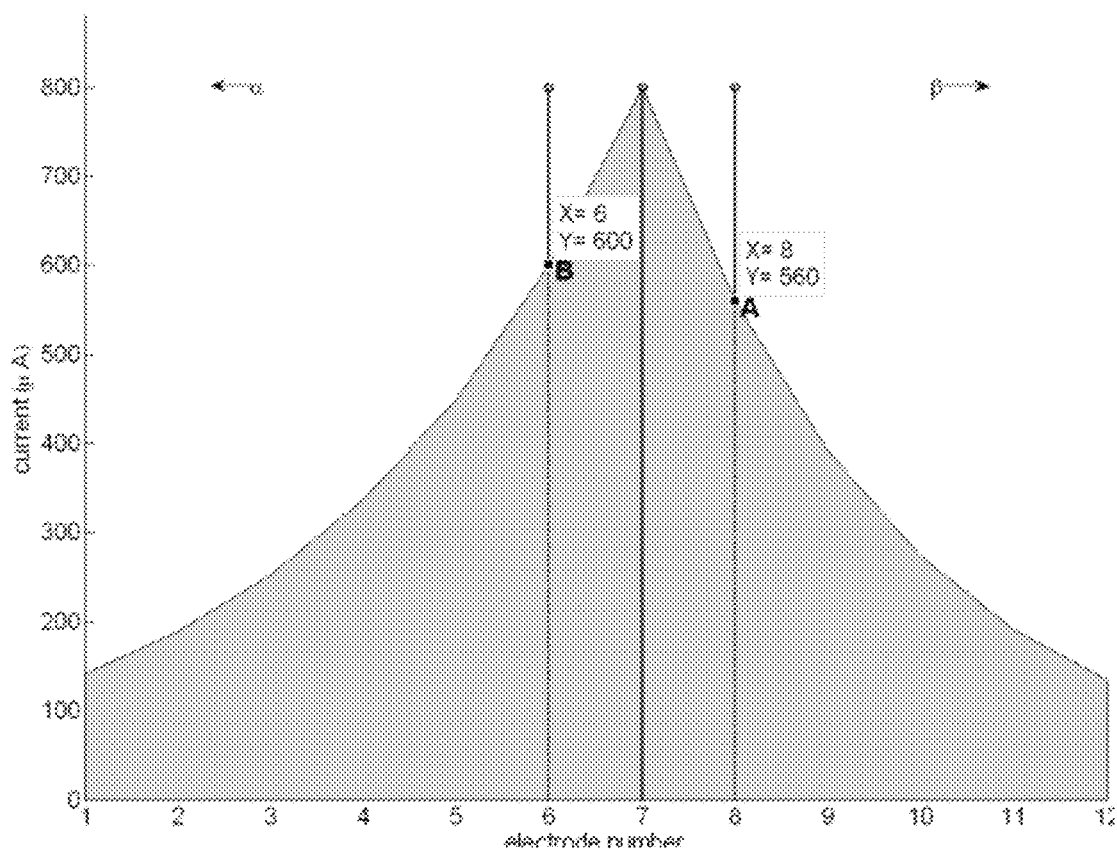
FIG. 3 shows an example of using electrode current spread for setting the initial MCL fit point.

For example with reference to FIG. 3, assume that Electrode 7 was the first electrode in the array to be fit to the MCL for the implanted patient. FIG. 3 shows an exemplary starting point for channel 8 is denoted as Point A, and an exemplary starting point for channel 6 is denoted as Point B. This will be continued for all channels until their respective MCLs are determined. More specifically, when electrode E7 is stimulated at 800 µA (MCL) as shown, assuming that α=0.75 and β=0.70, then the current spread will be as shown by the gray area under the exponential decay curves. (For convenience, only the current spread caused by the anodic stimulus phase of a biphasic pulse is depicted). In the given case, the next basally electrode E8 can only eliciting new neuronal structures if the released current exceeds Point A with 560 µA (800 µA*0.70, as given by Equation 3). On the next apically electrode E6 the initial fitting current needs to start at Point B with 600 µA (800 µA*0.75, as given by Equation 3).

The consideration of the current spread of the previously fitted electrodes leads to safe and effective starting points for the fitting of the next electrode. Here, safe means that the loudness at the starting point can not exceed the loudness (MCL) of the previously fitted electrode because no additional regions of neurons can be activated by this stimulation level. So with respect to FIG. 3, because the perceived loudness is primarily a function of the applied charge in neuronal structures, the perceptive loudness at these levels (E6=560 μA and E8=600 μA) cannot exceed the loudness as given for E7=800 μA because no additional neurons are activated, as stated before. Thus, the dotted lines in the grey area below Points A and B indicate unnecessary fitting current increments which are used in a traditional fitting procedure, but omitted here. Take for example the case of a flat-map fitting wherein the MCL of all 12 electrodes is 800 μA, then in a traditional fitting procedure (essentially corresponding to a calculation wherein α and β are set to 0) a range of 12*800 μA=960 μA has to be passed during the fitting procedure. By contrast, following the fit procedure as described above with a typical decay (α=0.75; β=0.70), then only 800 μA+11*200 μA=3000 μA has to be passed during the fitting when fitting is performed consecutively from base to apex. This indicates that a fitting can be performed in only ~30% of the time of a traditional fitting. In some embodiment, an additional safety distance to Point A or Point B may be introduced by starting some safety margin (e.g. 10%) below Points A and B for fitting electrode channels 8 and 6 respectively.

It may be that the most efficient specific sequence is to fit electrode channels going in the direction of shallower current decay. This is because when assuming a relatively even MCL profile across the electrode channels, then the starting point for fitting of the next electrode as derived from Equation 3 will be closer to the final MCL if the decay is shallower.

Embodiments of the present invention are only based on the electrically conductivity of the fluid and the resulting field distribution (channel crosstalk inside the scala tympani), and do not assume any particular kind of neural survival or neural responses. The amount of this channel crosstalk is directly affected by the distance between the electrodes (typically 0.75-2.4 mm). If some cases the amount of channel crosstalk may be higher, but this may not pose a problem because the initial fitting current starts at a lower level (assuming equal distances between electrodes). In addition, neural survival differences also should not be a problem—in the case that the region around a neighboring electrode delivers the biggest neural response (best neural survival), then the MCL of the current electrode is more related on the region of the neighboring electrode. In other words, when a fitting is performed for this electrode channel, all the neurons within the special profile are involved into the loudness percept. As long as a stimulus on any other electrode is below this profile, no louder percept can be elicited with this stimulus because no new/additional neurons are involved.

The approach described above may be more accurate than interpolating unmeasured channels based on MCL values of measured channels. Nevertheless, in some arrangements it may be useful to combine both approaches. And rather than modeling current spread based on exponential functions as described above, some embodiments of the present invention may use other appropriate current spread modeling functions. Or rather than using a mathematical function to model electrode current spread, the measured voltage profile of the telemetry measurement itself may be used directly after removing/canceling any signal artifacts (stimulation and recording artifacts). Or instead of using a current spread function to estimate the starting point of the next electrode channel in a fitting, a fixed percentage of the lowest previous measured MCL can be used, or a combination of both. In addition, current spread approach can also be used as the basis for estimating other implant system values such as electrically evoked compound action potential (eCAP), electrically evoked auditory brain stem responses (EABR), and electrically elicited stapedius reflex threshold (ESRT) values.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

For example, a pseudo code representation of a generic embodiment might be set forth as follows:

```
Process ChannelFitting
    determine MCL for first unfit electrode
    for each remaining unfit stimulation electrode
        set initial fitting current = f(CS_already_fit)
        determine MCL
```

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant fitting system for fitting an implanted cochlear implant electrode array having a plurality of stimulation electrodes to the implanted patient, the system comprising:

means for fitting a first unfit stimulation electrode by determining a most comfortable loudness (MCL) value; and means for determining an MCL value for at least one remaining unfit stimulation electrode starting from an initial fitting current value determined from an exponential decay curve representing current spread characteristics of MCL-level stimulation current of at least one already fit stimulation electrode.

2. A system according to claim 1, wherein the initial fitting current value further is based on a fixed percentage of the MCL value for an already fit stimulation electrode.

3. A system according to claim 1, wherein the at least one already fit stimulation electrode is adjacent in a more apical direction from the unfit stimulation electrode being fit.

4. A system according to claim 1, wherein the at least one already fit stimulation electrode is adjacent in a more basal direction from the unfit stimulation electrode being fit.

5. A computer program product implemented in a non-transitory computer readable storage medium for fitting an implanted cochlear implant electrode array having a plurality of stimulation electrodes to the implanted patient, the product comprising:

program code for fitting a first unfit stimulation electrode by determining a most comfortable loudness (MCL) value; and program code for determining an MCL value for at least one remaining unfit stimulation electrode starting from an initial fitting current value determined from an exponential decay curve representing current spread characteristics of MCL-level stimulation current of at least one already fit stimulation electrode.

6. A product according to claim 5, wherein the initial fitting current value further is based on a fixed percentage of the MCL value for an already fit stimulation electrode.

7. A product according to claim 5, wherein the at least one already fit stimulation electrode is adjacent in a more apical direction from the unfit stimulation electrode being fit.

8. A product according to claim 5, wherein the at least one already fit stimulation electrode is adjacent in a more basal direction from the unfit stimulation electrode being fit.

9. A method of fitting an implanted cochlear implant electrode array having a plurality of stimulation electrodes to the implanted patient, the method comprising:

fitting a first unfit stimulation electrode by determining a most comfortable loudness (MCL) value; and determining an MCL value for at least one remaining unfit stimulation electrode starting from an initial fitting current value determined from an exponential decay curve representing current spread characteristics of MCL-level stimulation current of at least one already fit stimulation electrode.

10. A method according to claim 9, wherein the initial fitting current value further is based on a fixed percentage of the MCL value for an already fit stimulation electrode.

11. A method according to claim 9, wherein the at least one already fit stimulation electrode is adjacent in a more apical direction from the unfit stimulation electrode being fit.

12. A method according to claim 9, wherein the at least one already fit stimulation electrode is adjacent in a more basal direction from the unfit stimulation electrode being fit.

* * * * *